United States Patent [19]

Schouten

[11] Patent Number: 4,485,241

[45] Date of Patent: Nov. 27, 1984

[54] REDUCTION OF INDOLE-2-CARBOXYLIC ACIDS TO INDOLINE-2-CARBOXYLIC ACIDS WITH LITHIUM, SODIUM, OR POTASSIUM IN AMMONIA

[75] Inventor: Henry G. Schouten, West Chester, Pa.

[73] Assignee: American Home Products Corporation, New York, N.Y.

[21] Appl. No.: 463,429

[22] Filed: Feb. 3, 1983

[51] Int. Cl.$^3$ ............................................ C07D 209/08
[52] U.S. Cl. ...................................................... 548/491
[58] Field of Search ........................................ 548/491

[56] References Cited

PUBLICATIONS

Sundberg, R. J. et al., The Chemistry of Indoles, pp. 129–131, (1970), Academic Press, N.Y.
Houlihan, W. J., Indoles, Part One, pp. 166–168, (1972) Wiley–Interscience, John Wiley & Sons, Inc., New York.
Krapcho, A. P. et al., American Chem. Soc., 81, 3658–3664, (1959).
Remers, W. A. et al., J. Amer. Chem. Soc., 89, 5513–5514, (1967).
Hudson et al., "The Synthesis and Chemistry of DL-Indoline-2-Carboxylic Acid", Aust. J. Chem., 20, 1935–1941 (1967).
Corey et al., "Studies in Asymmetric Synthesis of α-Amino Acids", J. Am. Chem. Soc., 92, 2476, 2480 (1970).
Robinson, B., "The Reduction of Indoles and Related Compounds", Chem. Reviews, 69, 785, 785–787 (1969).
Kaiser, E. M., Synthesis, pp. 391–415, 391 and 408–415 (1972).
Remers, et al., J. Org. Chem., 36, 279–284 (1971).
O'Brien, et al., J. Chem. Soc., pp. 4609–4612 (1960).

Primary Examiner—Nicholas S. Rizzo
Assistant Examiner—S. A. Gibson
Attorney, Agent, or Firm—Arthur G. Seifert

[57] ABSTRACT

Disclosed herein is an efficient and selective reduction of indole-2-carboxylic acids or esters to indoline-2-carboxylic acids using lithium, sodium, or potassium in liquid ammonia. The preferred process uses lithium in liquid ammonia with small amounts of a weak proton donor such as aniline added to the reaction mixture.

16 Claims, No Drawings

REDUCTION OF INDOLE-2-CARBOXYLIC ACIDS TO INDOLINE-2-CARBOXYLIC ACIDS WITH LITHIUM, SODIUM, OR POTASSIUM IN AMMONIA

Indoline-2-carboxylic acids are used as the starting material in the preparation of N-(3-mercapto-2-alkyl-1-oxopropyl)-2,3-dihydro-1H-indole-2-carboxylic acids and N-(2-[[1-(ethoxycarbonyl)-3-phenylpropyl]amino]-1-oxopropyl)-2,3-dihydro-1H-indole-2-carboxylic acids which exhibit pharmacological properties as angiotensin converting enzyme (ACE) inhibitors and as antihypertensive agents, as shown in U.S. Pat. Nos. 4,303,583 and 4,350,633, respectively.

Indoline-2-carboxylic acid (2,3-dihydro-1H-indole-2-carboxylic acid) was first described by Hudson and Robertson in the Australian Journal of Chemistry, 20, 1935 (1967). They obtained indoline-2-carboxylic acid by first reducing indole-2-carboxamide using phosphonium iodide and fuming hydriodic acid and then hydrolyzing the resulting indoline-2-carboxamide.

Subsequently, Corey et al., Journal of the American Chemical Society, 92, 2476–2488 (1970) described the reduction of indole-2-carboxylic acid ethyl ester to obtain indoline-2-carboxylic acid ethyl ester. Corey et al. used metallic tin and dry hydrogen chloride gas in ethanol in a high pressure sealed bomb for 36 hours to effect the reduction. In this method, the indoline-2-carboxylic acid ethyl ester is obtained first as a tin complex which is isolated and then treated with anhydrous ammonia to obtain the free ester. This ester must then be hydrolyzed in order to obtain the free acid desired as the starting material in the production of the described ACE inhibitors.

The preparation of indoline-2-carboxylic acids via the Corey et al. process thus has a number of drawbacks for both commercial and laboratory use. In the reduction step, a cumbersome sealed bomb and long reaction times are required due to the use of tin metal and excess hydrogen chloride gas (which generates hydrogen gas). Additionally, two steps are necessary to then obtain the desired indoline-2-carboxylic acid from the indoline-2-carboxylic acid ester tin complex. The treatment of the tin complex with anhydrous ammonia is also a cumbersome step since dry reagents must be used. In practice, it is difficult to remove all the tin from the ester even when dry conditions have been carefully maintained.

Applicant, on the other hand, has invented a reduction of indole-2-carboxylic acid to indoline-2-carboxylic acid which does not require tin metal or a sealed bomb. Applicant's process uses lithium, sodium, or potassium in liquid ammonia as the reducing agent. When indole-2-carboxylic acid is used as the starting material, the indoline-2-carboxylic acid is obtained directly in high purity and in yields of 80 percent. Particularly good results are obtained when a weak proton donor, such as aniline, is added to the reaction mixture. Plus, the reaction times are on the order of only 30 minutes using Applicant's process.

DETAILED DESCRIPTION OF THE INVENTION

Applicant's process for reducing an indole-2-carboxylic acid or ester of the formula:

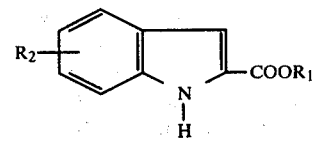

wherein $R_1$ is hydrogen or alkyl of 1–4 carbon atoms and $R_2$ is hydrogen, alkyl of 1–4 carbon atoms, alkoxy of 1–4 carbon atoms or hydroxy, to the corresponding indoline-2-carboxylic acid, which comprises reacting said indole-2-carboxylic acid or ester, dissolved in an inert solvent, with lithium, sodium, or potassium dissolved in liquid ammonia.

The inert solvent in which the indole-2-carboxylic acid or ester is dissolved may be tetrahydrofuran, 1,2-dimethoxy ethane, dioxane or an ether of 4–10 carbon atoms. Tetrahydrofuran is the preferred solvent, particularly when the starting material is indole-2-carboxylic acid. In the latter instance, the amount of tetrahydrofuran used as a solvent is about 450 to 650 ml. of tetrahydrofuran per 100 g. of indole-2-carboxylic acid. The larger amount is used where excessive evaporation from the reaction mixture is projected. (Note: Additional solvent is added from rinsing out the funnel after the indole-2-carboxylic acid solution is added to the Li-NH$_3$ solution).

Initially, slightly in excess of 2 moles of lithium, sodium or potassium per mole of indole-2-carboxylic acid or ester starting material are used. Usually, small amounts of the metal need to be added to maintain the reduction for the desired period, depending upon the purity of the starting material. In the case of lithium, 100 mg. portions are added as necessary to maintain the blue color of the reaction mixture. Typically, for 50 grams of indole-2-carboxylic acid under reduction, two additional 100 mg. portions of lithium are used. Lithium and sodium are the preferred metals for Applicant's reduction process, with lithium being most preferred.

As stated above, one advantage of Applicant's process is that reaction times are very short. 92 Percent yields may be achieved after only a 15 minute reaction period. Normally, when lithium is used as the reducing agent, the blue (active) color of the reaction mixture is maintained for about 30 minutes before it is destroyed, usually by the addition of excess ethanol. The reaction may be run at lower temperatures, less than $-33°$ C., without the evaporative cooling of ammonia. At such lower temperatures, (for example $-35°$ to $-45°$ C.) little or no ammonia would be lost and the reaction time could conveniently be shortened to 10–15 minutes.

After the reaction has been completed and stopped by the addition of excess ethanol, the temperature is gently raised to about 20° C. to boil off the bulk of the ammonia. Thereafter, the product is separated in an aqueous layer and isolated by adjusting the pH to 4.6–4.8. Where a greater amount of tetrahydrofuran (650 ml. per 100 grams of indole-2-carboxylic acid) is used initially, the ratio of methylene chloride per 100 grams of indole-2-carboxylic acid used in the separation step is increased from 1:5 to 1:7.

Applicant has found that the yield and purity of the product may be improved even further when a very weak proton donor is used as a moderate catalyst. Examples of such weak proton donors are aniline, toluidene, t-butyl alcohol, isopropyl alcohol and ethanol.

Aniline (pka=27) is preferred as a weak proton donor and is used at a ratio of 0.4 to 1.8 moles per mole of indole-2-carboxylic acid or ester starting material. Preferably, the ratio of aniline per mole of starting material is 0.4 to 0.9. The presence of a very weak proton donor in less than a one mole ratio is sufficient to make the reduction both efficient and specific for only the 2,3 double bond of the indole ring, giving even higher yields and purity than in the absence of the weak proton donor.

The following examples further illustrate the manner and best mode of carrying out the invention.

EXAMPLE 1

Indoline-2-Carboxylic Acid From Indole-2-Carboxylic Acid

To 5.0 g. (0.72 mole) of lithium 500 ml. liquid ammonia were added, and the mixture was stirred at a temperature of −30° C. to −35° C. for 15 minutes to affect solution. While at that temperature 50 g. (0.31 mole) indole-2-carboxylic acid dissolved in 225 ml. tetrahydrofuran were added as quickly as foaming permitted, using 25 ml. tetrahydrofuran as a rinse. The mixture was allowed to stir at −30° C. to −35° C. for 30 minutes after which the blue color was destroyed by the addition of 25 ml. ethyl alcohol. The bulk of the ammonia was removed by gentle heating, and 500 ml. water were added to dissolve the residual solids. While allowing to stir for 5 minutes, 250 ml. methylene chloride were added. The layers were then allowed to settle and were separated. The aqueous layer was cooled to 0°–5° C. and its pH was adjusted with 25% sulfuric acid to 4.6–4.8. The precipitate was allowed to stir for an additional 1 hour at 0°–5° C. The solids were filtered, washed with water and acetone, reslurried in acetone and dried. The weight of the product was 40.4 g. corresponding to a yield of 79.8%, m.p. 162–165.

EXAMPLE 2

Indoline-2-Carboxylic Acid From Indole-2-Carboxylic Acid

To 5.0 g. (0.72 mole) of lithium 1 L liquid ammonia was added and the mixture was stirred at a temperature of −30° C. to −35° C. until solution was affected. While at that temperature, 50 ml. (0.55 moles) aniline and a solution of 50 g. (0.31 mole) indole-2-carboxylic acid in 250 ml. tetrahydrofuran were added via an addition funnel as quickly as foaming permitted using 25 ml. tetrahydrofuran as a rinse. The blue color of the reaction mixture was maintained for 30 minutes, adding small amounts of lithium if required to maintain the blue color. After the mixture was stirred for 30 minutes at −30° C. or lower the blue color was destroyed by the addition of ethanol. The bulk of the ammonia was evaporated by heating the reaction mixture gently to about 20° C. About 600 ml. water was added to the mixture followed by 250 ml. methylene chloride. The aqueous layer was acidified with 25% aqueous sulfuric acid to a pH of approximately 4.8, at which point all the acid had precipitated. The mixture was stirred at 0°–5° C. for at least 1 hour, filtered and washed with water until sulfate free. After drying, the product weighed 42.1 g., which corresponds to a yield of 83.2%, m.p. 166°–169° C., assay titration 98.6%.

EXAMPLE 3

Indoline-2-Carboxylic Acid From Indole-2-Carboxylic Acid

To 15 g. (2.16 mole) of lithium 2 L liquid ammonia were added at a temperature of at least −30° C. until solution was affected. While at that temperature 150 ml. (1.65 moles) aniline and a solution of 150 g. (0.93 mole) indole-2-carboxylic acid in 675 ml. tetrahydrofuran were added by means of an addition funnel as quickly as foaming permitted using 75 ml. tetrahydrofuran as a wash. The blue color was maintained for 30 minutes, adding small amounts of lithium if required to keep the reaction mixture blue. The blue color was destroyed by the addition of ethanol. The reaction mixture was then heated to 20° C. to remove the bulk of the ammonia. To the residue 1650 ml. water were added followed by 750 ml. methylene chloride. The two layers were separated and the pH of the aqueous extract was adjusted to 4.6–4.8 by the addition of dilute sulfuric acid. The product, which had precipitated, was filtered after it had been allowed to stir at 0°–5° C. for at least 1 hour. After it was washed with water, it was dried to give a crude product in a yield of 136.1 g. or 89.6%. In order to remove any starting material present, it was reslurried in 350 ml. cold acetone and dried again. The product weighed 130.2 g. and corresponded to a yield of 85.8% based on the starting material, m.p. 166°–169° C., assay 99.3%.

EXAMPLE 4

Indoline-2-Carboxylic Acid From Indole-2-Carboxylic Acid

A 12 liter, 4-necked flask, marked at the 2.5 liter level, was fitted with a stirrer, a thermometer, an exit with a Gooch valve and an ammonia inlet. 2.6 Grams (3.74 moles) of lithium and then 2.5 liters of liquid ammonia were added to the flask. The liquid ammonia was stirred for 5–10 minutes until all of the lithium dissolved. While the temperature of the stirring mixture was maintained at −30° to −35° C., 125 ml. (1.375 moles) of aniline and then a solution of 250 grams (1.55 moles) of indole-2-carboxylic acid in 1625 ml. of tetrahydrofuran were added via an addition funnel as fast as foaming and gassing permitted. The addition funnel was then rinsed with another 125 ml. of tetrahydrofuran. The total addition time was 15 minutes. The temperature continued to be maintained at −30° to −35° C. by the addition of small amounts of liquid ammonia. The blue color of the reaction mixture was maintained for 30 minutes by the addition of two 100 mg. amounts of lithium. After this period, the blue color of the reaction mixture was destroyed by the cautious addition of 125 ml. of ethanol 3A anhydrous. The reaction mixture was then heated to about 20° C. with a warm water bath to drive off the bulk of the ammonia. 2750 ml. of water were then added to the resulting condensed mixture which was stirred for 10 minutes in order to dissolved the ammonium salt. 1750 ml. of methylene chloride were then added and the mixture was stirred slowly for 10 minutes. The two layers that formed were allowed to settle and then separated.

The aqueous layer was cooled to 5°–10° C. and then its pH was reduced to 4.6–4.8 by cautiously adding a 25% sulfuric acid solution while briskly stirring the mixture. About 600 ml. of the 25% sulfuric acid solution was required. The mixture was then stirred for one hour while holding the temperature at 5°–10° C. The solids were filtered out and washed twice with 250 ml. of water and twice with 75 ml. of acetone. The solids were then reslurried in 575 ml. of acetone in order to remove any unreacted indole-2-carboxylic acid, and the solid were again filtered out. These were sucked dry as possible and dried overnight in a vacuum oven at 45°–50° C. to a constant weight of indoline-2-carboxylic acid, m.p. 167°–170° C. (yield 225.0 g., 88.9%, assay titration 99.0%).

EXAMPLE 5

Indoline-2-Carboxylic Acid From Indole-2-Carboxylic Acid

A 5 liter, 4-necked flask equipped with a stirrer, a thermometer, an ammonia inlet, and a gas outlet with Gooch tubing was charged with 5 grams (0.72 moles) of lithium. 500 ml. of liquid ammonia was added and the mixture was stirred for 10 minutes to dissolve the lithium. 25 ml. (0.28 moles) of aniline were added, followed immediately by a solution of 50 grams (0.31 moles) of indole-2-carboxylic acid dissolved in 325 ml. of tetrahydrofuran. The addition funnel was rinsed with 25 ml. of tetrahydrofuran. The addition of the indole-2-carboxylic acid solution took about 5 minutes. The reaction mixture was stirred for 30 minutes at −35° C. The blue-green color held for 15–20 minutes and then faded. No additional lithium was added.

25 ml. of 3A ethanol was added to stop the reaction. The reaction mixture was warmed to 20° C., using a warm water bath, to drive off the bulk of the ammonia, precipitating solids, 500 ml. of water were then added and the mixture stirred for 10 minutes to dissolved the ammonium salts. Next the reaction mixture was extracted with 350 ml. of methylene chloride. The layers were separated. The aqueous layer was cooled and its pH adjusted to 4.6–4.8 by adding a 25 percent sulfuric acid solution. This mixture was stirred for 2 1/5 hours with a readjustment of the pH to 4.6–4.8 after ½ hour.

The product was collected by filration and rinsed with two 50 ml. portions of water and 2 25 ml. portions of cold acetone. The product was then slurried briefly (2 minutes) in 150 ml. of cold acetone, refiltered and rinsed with 25 ml. of cold acetone. The product was dried overnight in a vacuum oven at 45° C., yielding 46.2 grams (91.3%) of indoline-2-carboxylic acid, m.p. 170°–2° C.

EXAMPLE 6

Indoline-2-Carboxylic Acid From Indole-2-Carboxylic Acid

A 5 liter, 4-necked flask equipped with a stirrer, a thermometer, an ammonia inlet tube, and a gas outlet with Gooch tubing was charged with 5 grams (0.72 moles) of lithium. 500 ml. of liquid ammonia was added and the mixture was stirred for 10 minutes to dissolved the lithium. 25 ml. (0.28 moles) of aniline was added, followed immediately by the addition of a solution of 50 grams (0.31 moles) of indole-2-carboxylic acid dissolved in 325 ml. of tetrahydrofuran. The addition funnel was rinsed with 25 ml. of tetrahydrofuran. This addition took about 5 minutes. The blue-green color disappeared a few minutes after the addition and 0.2 grams of lithium was added. The blue-green color was maintained for about 10 more minutes. No additional lithium was added. The reaction mixture was stirred for a total of 30 minutes, maintaining the temperature at −35° C. 25 ml. of ethanol was then added to end the reaction.

The reaction mixture as warmed to 20° C. to drive off the bulk of the ammonia. Thereafter, 500 ml. of water was added and the mixture stirred for 10 minutes to dissolve the ammonium salts. The reaction mixture was extracted with 350 ml. of methylene chloride, and the settled layers were separated. The pH of the aqueous layers was then adjusted to pH 46–48 by the addition of a 25 percent solution of sulfuric acid. This mixture was stirred at 5°–10° C. for 3 hours, readjusting the pH to 4.6–4.8 after 30 minutes.

The product was collected by filtration and then rinsed twice with 50 ml. of water and twice with 25 ml. of cold acetone. The product was then slurried in 150 ml. of cold acetone, refiltered, and rinsed with 25 ml. of cold acetone. The product was dried overnight in a vacuum oven at 45° C., yielding 40.5 g. (80.0%) of indoline-2-carboxylic acid, m.p. 169°–172° C.

What is claimed is:

1. A process for reducing an indole-2-carboxylic acid or ester of the formula:

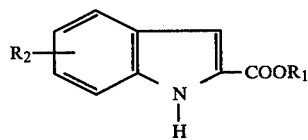

wherein $R_1$ is hydrogen or alkyl of 1–4 carbon atoms and $R_2$ is hydrogen, alkyl of 1–4 carbon atoms, alkoxy of 1–4 carbon atoms or hydroxy, to the corresponding indoline-2-carboxylic acid, which process comprises reacting said indole-2-carboxylic acid, dissolved in an inert solvent, with lithium, sodium, or potassium dissolved in liquid ammonia.

2. A process according to claim 1 in which the inert solvent is chosen from tetrahydrofuran, 1,2-dimethoxy ethane, dioxane and an ether of 4–10 carbon atoms.

3. A process according to claim 1 in which the inert solvent is tetrahydrofuran.

4. A process according to claim 1 wherein the metal reactant is lithium or sodium.

5. A process according to claim 1 wherein the metal reactant is lithium.

6. A process according to claim 1 which is carried out in the presence of a very weak proton donor.

7. A process according to claim 6 wherein the weak proton donor is aniline.

8. A process according to claim 7 in which the amount of aniline used is 0.4–0.9 moles per mole of the indole-2-carboxylic acid or ester starting material.

9. A process according to claim 1 wherein indole-2-carboxylic acid is reduced to indoline-2-carboxylic acid.

10. A process for reducing indole-2-carboxylic acid to indoline-2-carboxylic acid, which process comprises reacting indole-2-carboxylic acid, dissolved in an inert solvent, with lithium or sodium dissolved in liquid ammonia.

11. A process according to claim 10 in which the inert solvent is chosen from tetrahydrofuran, 1,2-dimethoxy ethane, dioxane and an ether of 4–10 carbon atoms.

12. A process according to claim 10 in which the inert solvent is tetrahydrofuran.

13. A process according to claim 10 wherein the metal reactant is lithium.

14. A process according to claim 10 which is carried out in the presence of a very weak proton donor.

15. A process according to claim 14 wherein the weak proton donor is aniline.

16. A process according to claim 1 which is carried out in the presence of aniline in a ratio of 0.4–0.9 moles of aniline per mole of the indole-2-carboxylic acid starting material.

* * * * *